US00PP14340P29

(12) United States Plant Patent
Hoogendoorn

(10) Patent No.: US PP14,340 P2
(45) Date of Patent: Dec. 2, 2003

(54) ALSTROEMERIA PLANT NAMED 'ZANVELVET'

(50) Latin Name: *Alstroemeria hybrida*
Varietal Denomination: Zanvelvet

(75) Inventor: Cornelis Arie Hoogendoorn, Rijsenhout (NL)

(73) Assignee: Van Zanten Plants B.V., Hillegom (NL)

( * ) Notice: Subject to any disclaimer, the term of this patent is extended or adjusted under 35 U.S.C. 154(b) by 0 days.

(21) Appl. No.: 10/287,078

(22) Filed: Nov. 4, 2002

(51) Int. Cl.[7] ..... A01H 5/00
(52) U.S. Cl. ..... Plt./309
(58) Field of Search ..... Plt./309

*Primary Examiner*—Kent Bell
(74) *Attorney, Agent, or Firm*—C. A. Whealy

(57) ABSTRACT

A new and distinct cultivar of Alstroemeria plant named 'Zanvelvet', characterized by its erect flowering stems; red purple and white bi-colored flowers with dark purple-colored spots and stripes; and excellent postproduction longevity.

1 Drawing Sheet

Botanical classification/cultivar designation: *Alstroemeria hybrida* cultivar 'Zanvelvet'.

BACKGROUND OF THE INVENTION

The present Invention relates to a new and distinct cultivar of Alstroemeria plant, botanically known as *Alstroemeria hybrida,* commercially used as a cut flower Alstroemeria, and hereinafter referred to by the name 'Zanvelvet'.

The new Alstroemeria is a product of a planned breeding program conducted by the Inventor in Hillegom, The Netherlands. The objective of the breeding program was to develop new cut flower Alstroemeria cultivars with strong plant growth, attractive flower colors and excellent postproduction longevity.

The new Alstroemeria originated from a cross made by the Inventor in April, 1995 in Hillegom, The Netherlands, of a proprietary *Alstroemeria hybrida* selection identified as 94547-1, not patented, as the female, or seed, parent with a proprietary *Alstroemeria hybrida* selection identified as 94676-4, not patented, as the male, or pollen, parent. The new Alstroemeria was discovered and selected by the Inventor as a flowering plant within the progeny of the stated cross in a controlled environment in Hillegom, The Netherlands in April, 1996.

Asexual reproduction of the new cultivar by root divisions taken in a controlled environment in Hillegom, The Netherlands, since June, 1996, has shown that the unique features of this new Alstroemeria are stable and reproduced true to type in successive generations of asexual propagation.

SUMMARY OF THE INVENTION

Plants of the cultivar Zanvelvet have not been observed under all possible environmental conditions. The phenotype may vary somewhat with variations in environment such as temperature and light intensity without, however, any variance in genotype.

The following traits have been repeatedly observed and are determined to be the unique characteristics of 'Zanvelvet'. These characteristics in combination distinguish 'Zanvelvet' as a new and distinct cultivar:

1. Erect flowering stems.
2. Red purple and white bi-colored flowers with dark purple-colored spots and stripes.
3. Excellent postproduction longevity.

Plants of the new Alstroemeria are most similar to plants of the parent selections. However, plants of the new Alstroemeria differ from plants of the parents in flower coloration as plants of the female parent have purple-colored flowers and plants of the male parent have dark red-colored flowers.

Plants of the new Alstroemeria can be compared to plants of the cultivar Granada, not patented. In side-by-side comparisons conducted in Rijsenhout, The Netherlands, plants of the new Alstroemeria differed primarily from plants of the cultivar Granada as plants of the cultivar Granada had pink-colored flowers.

BRIEF DESCRIPTION OF THE PHOTOGRAPH

The accompanying colored photograph illustrates the overall appearance of the new Alstroemeria, showing the colors as true as it is reasonably possible to obtain in colored reproductions of this type. Colors in the photograph may differ slightly from the color values cited in the detailed botanical description which accurately describe the colors of the new Alstroemeria. The photograph comprises a side perspective view of typical flowers of 'Zanvelvet'.

DETAILED BOTANICAL DESCRIPTION

The aforementioned photograph, following observations and measurements describe plants of the new Alstroemeria grown in Rijsenhout, The Netherlands in a glass-covered greenhouse in ground beds. During the production of the plants, day temperatures ranged from 15 to 20° C., night temperatures ranged from 10 to 15° C., soil temperatures of 14° C. and light levels were about 5,000 lux. Plants used for the photograph and description were about 12 months from planting root divisions. The photograph and the description were taken during March and April, 2002.

Color references are made to The Royal Horticultural Society Colour Chart, 1995 Edition, except where general terms of ordinary dictionary significance are used.

Botanical classification: *Alstroemeria hybrida* cultivar Zanvelvet.

Parentage:

*Female parent.*—Proprietary *Alstroemeria hybrida* selection identified as 94547-1, not patented.

*Male parent.*—Proprietary selection of *Alstroemeria hybrida* identified as 94676-4, not patented.

Propagation:

*Type.*—By root divisions.

*Root description.*—Fibrous, fleshy, thick; white, close to 155D, in color.

*Rooting habit.*—Freely branching.

*Rhizomes.*—Shape: Elongate; rounded. Length: About 10 to 30 cm. Diameter: About 0.3 to 1 cm. Texture: Smooth. Color: Close to 155D.

Plant description:

*Plant habit.*—Upright; freely basal branching, bushy appearance.

*Time from planting to harvest of cut flowers.*—About 80 to 90 days.

*Number of flowering stems produced per year.*—About 154 to 180.

*Plant height.*—About 90 to 144 cm.

*Plant diameter* (*spread*).—About 25 to 30 cm.

*Flowering stem description.*—Aspect: Erect. Length: About 120 cm. Diameter: About 4.6 to 9 mm. Internode length: About 3 to 9 cm. Strength: Strong. Texture: Pubescent. Color: Close to 144A to 144B.

*Foliage description.*—Leaves asymmetrical; sessile. Length: About 12 to 19 cm. Width: About 2.5 to 4 cm. Shape: Lanceolate. Apex: Acute. Base: Attenuate. Margin: Entire. Texture, upper and lower surfaces: Glabrous. Venation pattern: Parallel. Color: Young and fully developed foliage, upper surface: Close to 137A; moderately glossy. Young and fully developed foliage, lower surface: Close to 137C. Venation: Upper surface, close to 137A; lower surface, close to 137C.

Flower description:

*Flower type and habit.*—Single cup-shaped flowers arranged in compound umbels. Perianth segments separate. Freely and continuously flowering. Flowers not persistent.

*Natural flowering season.*—Flowering continuous during the spring in The Netherlands.

*Fragrance.*—None detected.

*Flower longevity on the plant.*—About four weeks.

*Flower longevity as a cut flower.*—About 15 to 20 days.

*Flower buds* (*showing color*).—Length: About 2 to 4 cm. Diameter: About 1 to 2 cm. Shape: Roughly ovoid. Color: Close to 60A.

*Umbel height.*—About 15 to 25 cm.

*Umbel diameter.*—About 20 to 30 cm.

*Number of flowers per umbel.*—About 12 to 28.

*Flower height* (*length*).—About 5.5 to 7 cm.

*Flower diameter.*—About 5 to 7 cm.

*Flower depth.*—About 6 to 7 cm.

*Perianth.*—Arrangement: Six arranged in two whorls, each whorl with two lateral and one median segments. Size: Inner perianth: Length: Laterals, about 5.5 to 6.5 cm; median, 6 to 7 cm. Width: Laterals, about 1.5 to 2 cm; median, about 1.7 to 2.3 cm. Outer perianth: Length, laterals and median: About 6 to 7 cm. Width: Laterals, about 3 to 3.5 cm; median, about 2.5 to 3.5 cm. Shape: Inner perianth, all segments: Oblanceolate. Outer perianth, all segments: Obovate. Apex: Inner perianth, all segments: Acute. Outer perianth, all segments: Bracket-shaped. Base, inner and outer perianths, all segments: Attenuate. Margin, inner and outer perianths, all segments: Entire; slightly undulate. Texture, inner and outer perianths, all segments: Smooth, glabrous; velvety. Color: Inner perianth: When opening and fully opened, upper surface: Laterals: Towards apex and base, close to 60A; mid-section, close to 155A; spots and stripes, close to 187A; at apex, close to 155D. Median: Close to 60A; spots and stripes, close to 187A; at apex, close to 155D. When opening and fully opened, lower surface, laterals and median: Close to 60A. Outer perianth, when opening and fully opened, upper and lower surfaces, laterals and median: Close to 60A; at apex, close to 146A.

*Pedicels.*—Length: About 2 to 3 cm. Diameter: About 2 to 4 mm. Strength: Strong. Angle: About 30 to 60° from vertical. Texture: Smooth, glabrous. Color: Close to 137B.

*Reproductive organs.*—Stamens: Quantity per flower: Six. Anther shape: Elliptical. Anther length: About 8 mm. Anther diameter: About 3 mm. Anther color: Close to 185A. Pollen amount: Scarce. Pollen color: Close to 202B. Pistils: Quantity per flower: One. Style length: About 4 to 5 cm. Stigma color: Light purple. Ovary color: Close to 144A.

*Fruit.*—Shape: Globular. Color: Brown.

Disease/pest resistance: Plants of the new Alstroemeria have not been observed to be resistant to pathogens and pests common to Alstroemerias.

Temperature tolerance: Plants of the new Alstroemeria have been observed to tolerate temperatures from −5 to 40° C.

It is claimed:

1. A new and distinct cultivar of Alstroemeria plant named 'Zanvelvet', as illustrated and described.

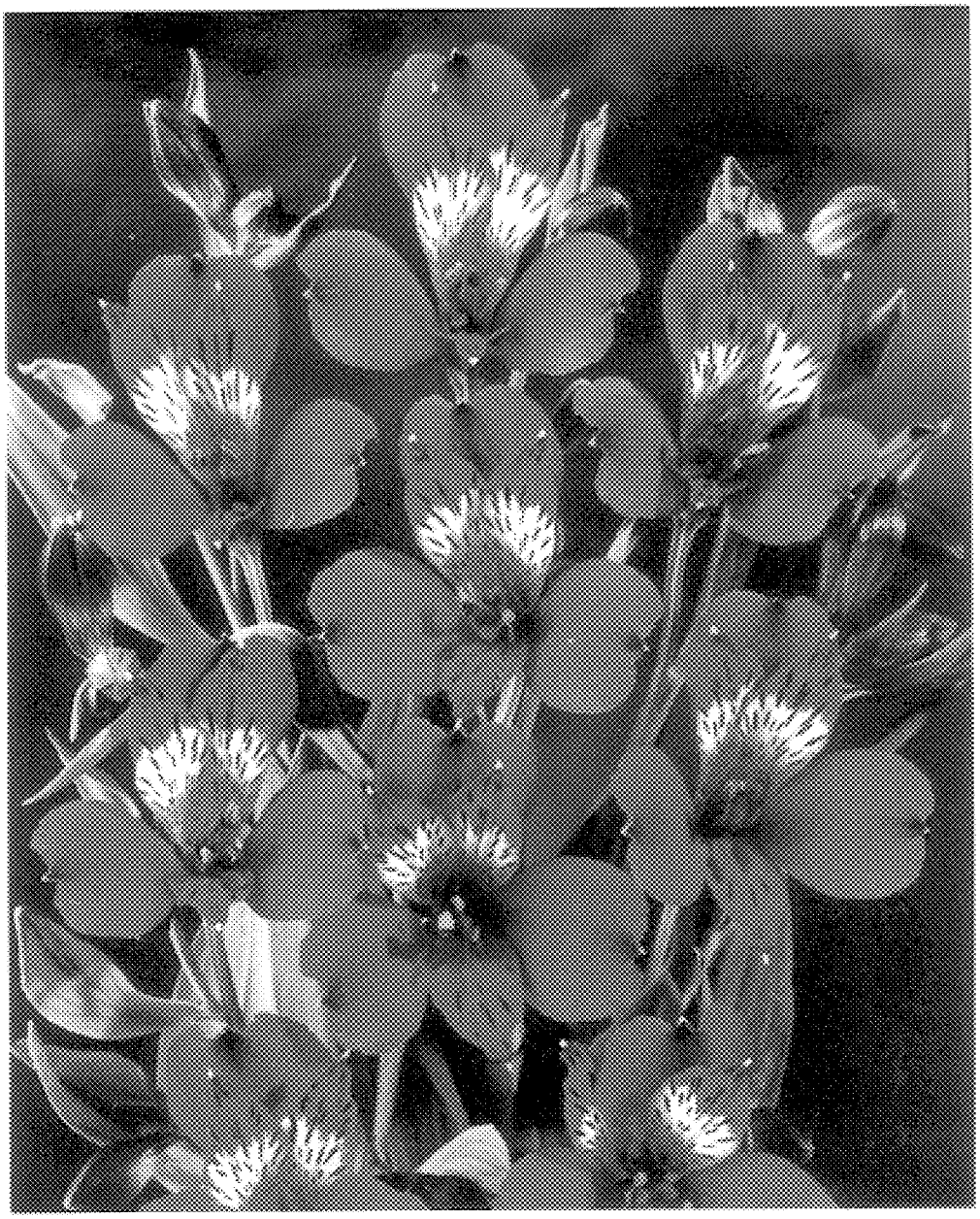

* * * * *